United States Patent
Wang et al.

(10) Patent No.: US 10,501,468 B2
(45) Date of Patent: Dec. 10, 2019

(54) METHOD FOR PREPARING INTERMEDIATE OF 6-ARYLAMINOPYRIDONECARBOXAMIDE COMPOUND AS MEK INHIBITOR

(71) Applicants: CHIA TAI TIANQING PHARMACEUTICAL GROUP CO., LTD., Jiangsu (CN); CENTAURUS BIOPHARMA CO., LTD., Bejing (CN)

(72) Inventors: Lulu Wang, Jiangsu (CN); Fei Liu, Jiangsu (CN); Yizhong Zhu, Jiangsu (CN); Hongying Zhang, Jiangsu (CN)

(73) Assignees: CHIA TAI TIANQING PHARMACEUTICAL GROUP CO., LTD, Jiangsu (CN); CENTAURUS BIOPHARMA CO., LTD., Beijing (CN)

( * ) Notice: Subject to any disclaimer, the term of this patent is extended or adjusted under 35 U.S.C. 154(b) by 0 days.

(21) Appl. No.: 16/324,876

(22) PCT Filed: Aug. 11, 2017

(86) PCT No.: PCT/CN2017/097045
§ 371 (c)(1),
(2) Date: Feb. 11, 2019

(87) PCT Pub. No.: WO2018/028665
PCT Pub. Date: Feb. 15, 2018

(65) Prior Publication Data
US 2019/0177335 A1    Jun. 13, 2019

(30) Foreign Application Priority Data

Aug. 12, 2016 (CN) .......................... 2016 1 0666408

(51) Int. Cl.
C07D 491/048    (2006.01)
C07C 335/32     (2006.01)

(52) U.S. Cl.
CPC ........ C07D 491/048 (2013.01); C07C 335/32 (2013.01)

(58) Field of Classification Search
None
See application file for complete search history.

(56) References Cited

U.S. PATENT DOCUMENTS 4,011,342 A     3/1977  Schwartz et al.
2014/0080804 A1  3/2014  Xiao et al.

FOREIGN PATENT DOCUMENTS

| CA | 1187888 | 5/1985 |
| CN | 1033624 | 7/1989 |
| CN | 102020651 | 4/2011 |
| CN | 105315293 | 2/2016 |
| EP | 0075205 | 3/1983 |
| WO | WO 89/00563 | 1/1989 |

OTHER PUBLICATIONS

International Search Report and Written Opinion in International Application No. PCT/CN2017/097045, dated Nov. 17, 2017, 9 pages.

*Primary Examiner* — Zinna Northington Davis
(74) *Attorney, Agent, or Firm* — Fish & Richardson P.C.

(57) ABSTRACT

Provided is a method for preparing an intermediate of 6-arylaminopyridonecarboxamide compound as an MEK inhibitor, comprising preparing a compound of formula (III) as an intermediate of 6-arylaminopyridonecarboxamide compound using a compound of formula V as a raw material.

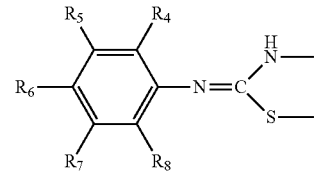

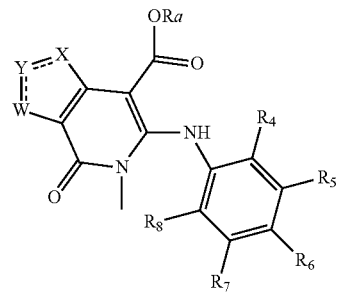

18 Claims, No Drawings

METHOD FOR PREPARING INTERMEDIATE OF 6-ARYLAMINOPYRIDONECARBOXAMIDE COMPOUND AS MEK INHIBITOR

CROSS REFERENCE TO RELATED APPLICATION

The present application claims the priority and benefit of the Chinese invention patent application No. 201610666408.1 filed with the China National Intellectual Property Administration on Aug. 12, 2016, which is incorporated herein by reference in its entirety.

TECHNICAL FIELD

The present application relates to a method for preparing an intermediate of 6-arylaminopyridonecarboxamide compound.

BACKGROUND

CN102020651A discloses 6-arylaminopyridonecarboxamide compound represented by formula I as a MEK inhibitor, and a method for treating a MEK-mediated conditions or disorders in a mammal (including a human), such as inflammatory diseases, infections, autoimmune diseases, stroke, ischemia, non-cancer hyperproliferative diseases, tumors, and other diseases.

Formula I

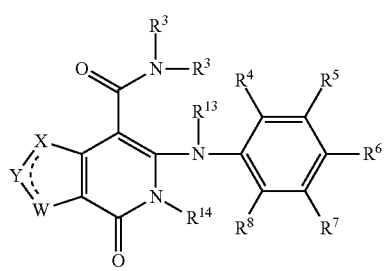

CN102020651A further discloses a method for preparing a compound of formula I by using a carbodiimide compound as a starting material, such as a preparation method of 6-(2-chloro-4-iodophenylamino)-N-(2-hydroxyethoxy)-5-methyl-4-oxo-4,5-dihydrofuro[3,2-c]pyridine-7-carboxamide as shown in scheme 1, Scheme 1

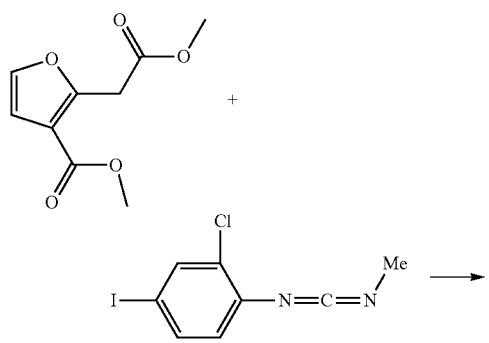

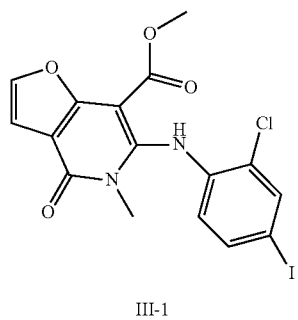

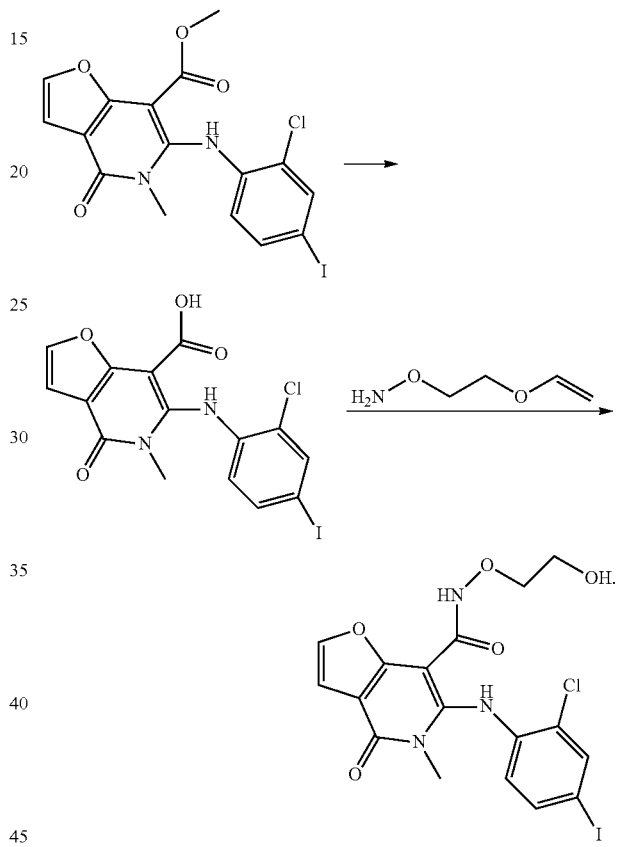

In this scheme, carbodiimide is very easy to absorb moisture to form urea, and accordingly it is difficult to store. There are extremely strict requirements for the storage environment of reaction raw materials during the scale-up production, thereby increasing the production costs. Furthermore, after absorbing moisture, carbodiimide would introduce impurities into the reaction, and the reaction product needs to be purified to remove these impurities, thereby decreasing the yield and increasing the production costs. In addition, this synthesis route needs the use of sodium hydride. Sodium hydride easily causes burning and explosion, is irritating to the human body, and easy to cause skin burns, and consequently, there is a greater potential safety hazard during the scale-up production. Moreover, sodium hydride causes great damage to the environment, and is not conducive to large-scale production.

Therefore, there is a need to find a new preparation method suitable for the industrial production of an intermediate of a compound of formula I.

SUMMARY

In an aspect, the present application provides a method for preparing a compound of formula III, comprising reacting a compound of formula IV with a compound of formula V,

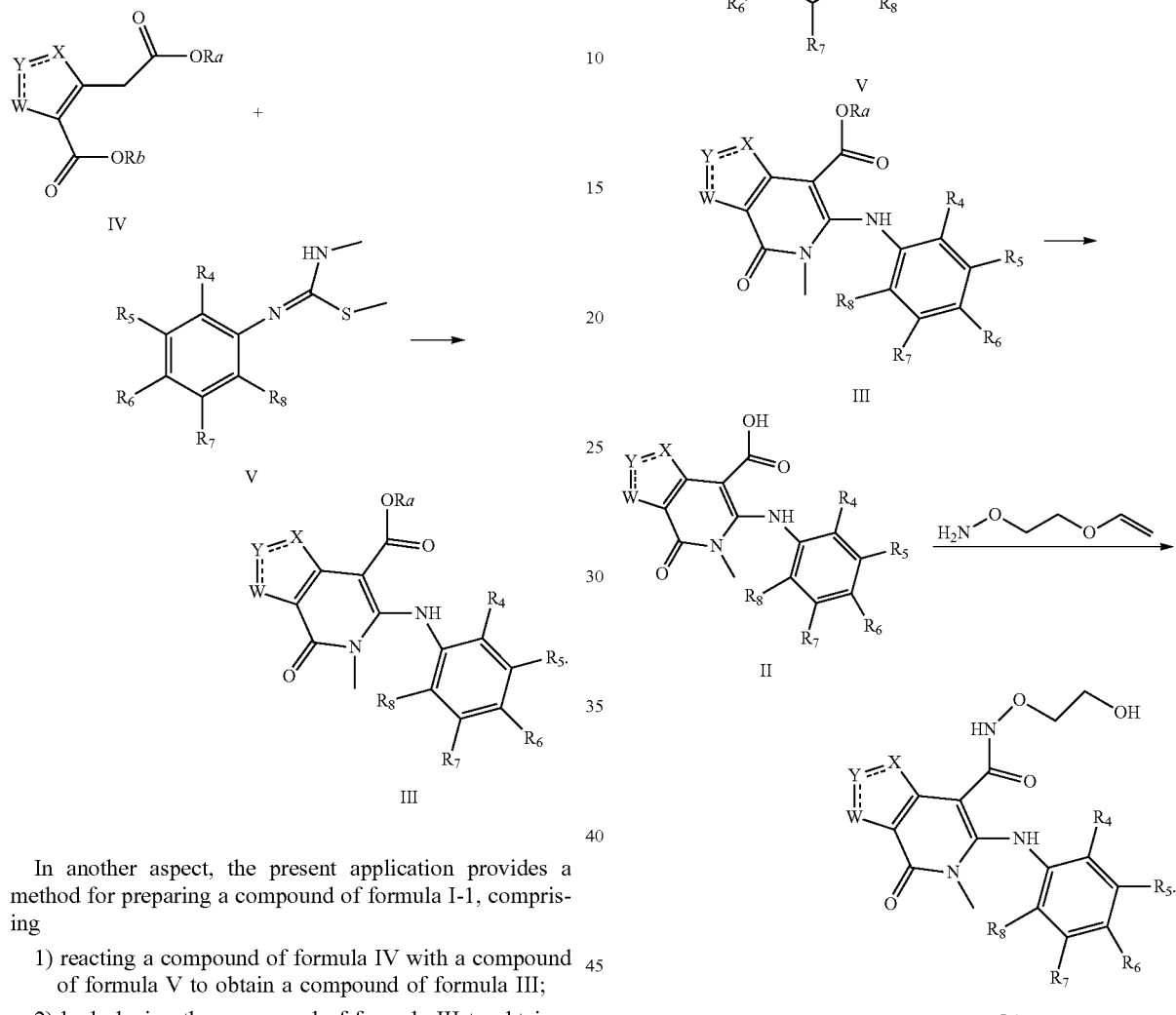

In another aspect, the present application provides a method for preparing a compound of formula I-1, comprising 1) reacting a compound of formula IV with a compound of formula V to obtain a compound of formula III;
2) hydrolyzing the compound of formula III to obtain a compound of formula II;
3) reacting the compound of formula II with O-(2-(vinyloxy)ethyl)hydroxylamine followed by hydrolysis to obtain the compound of formula I-1; or
4) reacting the compound of formula III with O-(2-(vinyloxy)ethyl)hydroxylamine followed by hydrolysis to obtain the compound of formula I-1;

In still another aspect, the present application further relates to a compound of formula V and use of the compound of formula V in the preparation of a compound of formula I-1,

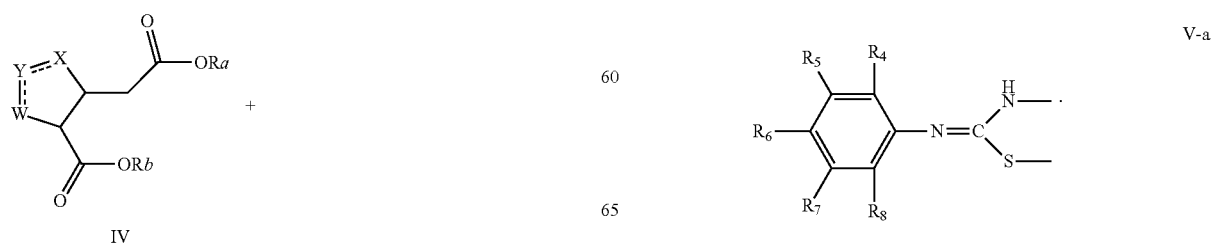

In some embodiments of the present application, $R_a$ and $R_b$ are each independently selected from the group consisting of hydrogen and $C_1$-$C_6$ alkyl;

$$X = Y = W$$

represents X—Y=W or X=Y—W; X and W are independently selected from the group consisting of N, O, S, and $CR_2$; Y is $CR_1$; and $R_1$ is selected from the group consisting of H and $C_1$-$C_6$ alkyl, wherein the alkyl is optionally substituted with a substituent independently selected from the group consisting of halo, hydroxyl, —$NH_2$, —$NH(C_1$-$C_6$ alkyl), —$N(C_1$-$C_6$ alkyl)$_2$, and $C_1$-$C_6$ heterocyclic group; $R_2$ is selected from the group consisting of H and $C_1$-$C_6$ alkyl; $R_4$, $R_5$, $R_6$, $R_7$, and $R_8$ are independently selected from the group consisting of H, halo, $SR_9$, and $OR_9$; and each $R_9$ is independently selected from the group consisting of hydrogen and $C_1$-$C_{10}$ alkyl.

DETAILED DESCRIPTION OF THE INVENTION

In the following description, certain specific details are included to provide a thorough understanding of various disclosed embodiments. However, those skilled in the relevant art will recognize that the embodiments may be practiced without one or more of these specific details, or with other methods, components, materials, and the like.

Unless the context requires otherwise, throughout the specification and claims which follow, the term "comprise" and English variations thereof, such as "comprises" and "comprising", are to be construed in an open and inclusive sense, that is as, "including, but not limited to".

Reference throughout this specification to "one embodiment", or "an embodiment", or "another embodiment", or "some embodiments" means that a particular referent element, structure, or characteristics described in connection with the embodiment is included in at least one embodiment. Accordingly, the appearances of the phase "in one embodiment", or "in an embodiment", or "in another embodiment", or "in some embodiments" in various places throughout this specification are not necessarily all referring to the same embodiment. In addition, the particular elements, structures, or characteristics may be combined in any suitable manner in one or more embodiments.

It should be noted that, as used in this specification and the appended claims, the singular forms "a", "an" and "the" include plural referents unless the content clearly dictates otherwise. Thus, for example, reference to a reaction in which "a catalyst" is involved includes a single catalyst, or two or more catalysts. Unless otherwise explicitly specified herein, it should also be noted that the term "or" is generally employed in its sense including "and/or" unless the content clearly dictates otherwise.

In an aspect, the present application provides a method for preparing a compound of formula III, comprising reacting a compound of formula IV with a compound of formula V,

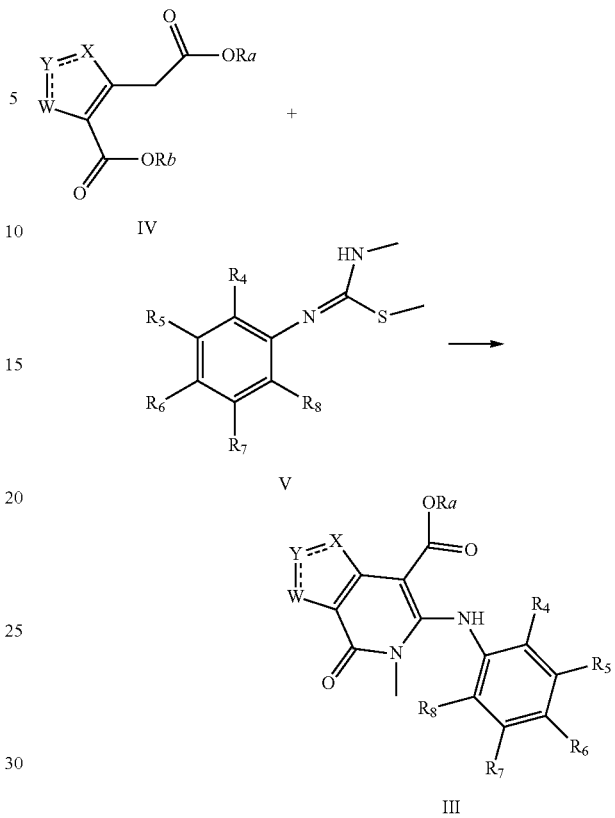

wherein $R_a$ and $R_b$ are each independently selected from the group consisting of hydrogen and $C_1$-$C_6$ alkyl;

$$X = Y = W$$

represents X—Y=W or X=Y—W;
X and W are independently selected from the group consisting of N, O, S, and $CR_2$;
Y is $CR_1$; and
$R_1$ is selected from the group consisting of H and $C_1$-$C_6$ alkyl, wherein the alkyl is optionally substituted with a substituent independently selected from the group consisting of halo, hydroxyl, —$NH_2$, —$NH(C_1$-$C_6$ alkyl), —$N(C_1$-$C_6$ alkyl)$_2$, and $C_1$-$C_6$ heterocyclic group;
$R_2$ is selected from the group consisting of H and $C_1$-$C_6$ alkyl;
$R_4$, $R_5$, $R_6$, $R_7$, and $R_8$ are independently selected from the group consisting of H, halo, $SR_9$, and $OR_9$; and
each $R_9$ is independently selected from the group consisting of hydrogen and $C_1$-$C_{10}$ alkyl.

In some embodiments of the present application, $R_a$ and $R_b$ are each independently $C_1$-$C_6$ alkyl. In some typical embodiments of the present application, $R_a$ and $R_b$ are each independently selected from the group consisting of methyl, ethyl, n-propyl, isopropyl, n-butyl, isobutyl, and tert-butyl. In some more typical embodiments of the present application, $R_a$ and $R_b$ are each independently selected from the group consisting of methyl, ethyl, and n-propyl. In some still more typical embodiments of the present application, $R_a$ and $R_b$ are methyl or ethyl.

In some embodiments of the present application, X is O or S, and W is $CR_2$.

In some embodiments of the present application, $R_4$, $R_5$, $R_6$, $R_7$, and $R_8$ are independently selected from the group consisting of H and halo. In some typical embodiments of the present application, one of $R_4$ and $R_8$ is fluoro or chloro, and $R_6$ is iodo.

In some embodiments of the present application, $R_a$ and $R_b$ are each independently selected from the group consisting of methyl and ethyl; X is O; Y is CH; W is CH; $R_4$ is chloro; $R_6$ is iodo; and each of $R_5$, $R_7$, and $R_8$ is hydrogen.

In some embodiments of the present application, the compound of formula IV reacts with the compound of formula V in a first solvent selected from the group consisting of tetrahydrofuran, dichloromethane, ethyl acetate, N,N-dimethylformamide, acetone, N,N-dimethylacetamide, N-methyl pyrrolidone, dimethyl sulfoxide, and a mixture thereof. Preferably, the first solvent is selected from the group consisting of tetrahydrofuran, N,N-dimethylformamide, acetone, N-methyl pyrrolidone, and a mixture thereof. More preferably, the first solvent is tetrahydrofuran, acetone, or a mixture thereof.

In some embodiments of the present application, the compound of formula IV reacts with the compound of formula V in the presence of a first base. Preferably, the first base is selected from the group consisting of NaHMDS, LiHMDS, KHMDS, lithium diisopropylamide, tert-butyl lithium, n-butyl lithium, potassium tert-butoxide, sodium methoxide, and a mixture thereof. More preferably, the first base is selected from the group consisting of NaHMDS, LiHMDS, tert-butyl lithium, and a mixture thereof. Still more preferably, the first base is NaHMDS or LiHMDS.

In some embodiments of the present application, the present application provides a method for preparing a compound of formula III, comprising reacting a compound of formula IV with a compound of formula V in the presence of a first base and a first solvent to obtain the compound of formula III,

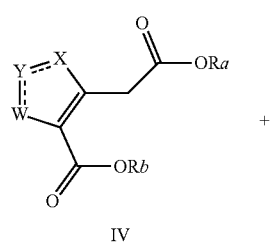

IV

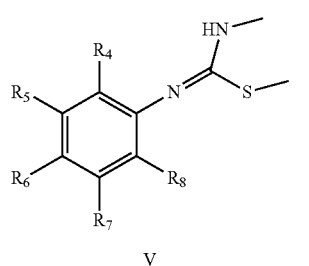

V

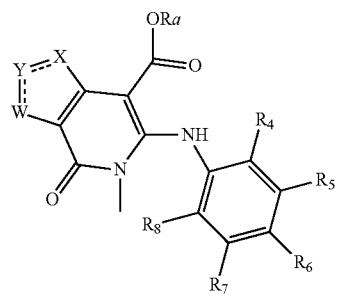

III wherein $R_a$, $R_b$, $$X\!=\!\!=\!Y\!=\!\!=\!W,$$

X, W, Y, $R_4$, $R_5$, $R_6$, $R_7$, and $R_8$ as well as the first base and the first solvent are as defined hereinabove.

In some embodiments of the present application, a molar ratio of the compound of formula IV to the first base is 1:1~5; preferably, the molar ratio of the compound of formula IV to the first base is 1:1~3; and more preferably, the molar ratio of the compound of formula IV to the first base is 1:1~1.5.

In some embodiments of the present application, a molar ratio of the compound of formula IV to the compound of formula V is 1~5:1; preferably, the molar ratio of the compound of formula IV to the compound of formula V is 1~3:1; and more preferably, the molar ratio of the compound of formula IV to the compound of formula V is 1.5~2:1.

In some embodiments of the present application, the compound of formula IV reacts with the compound of formula V at a temperature of 45° C. to 70° C.; and preferably, the compound of formula IV reacts with the compound of formula V at a temperature of 50° C. to 65° C.

In another aspect, the present application provides a method for preparing a compound of formula I-1, comprising 1) reacting a compound of formula IV with a compound of formula V to obtain a compound of formula III;
2) hydrolyzing the compound of formula III to obtain a compound of formula II; and
3) reacting the compound of formula II with O-(2-(vinyloxy)ethyl)hydroxylamine followed by hydrolysis to obtain the compound of formula I-1,

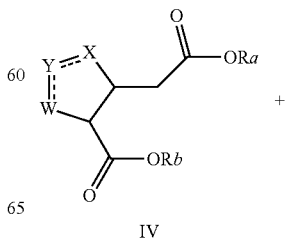

IV

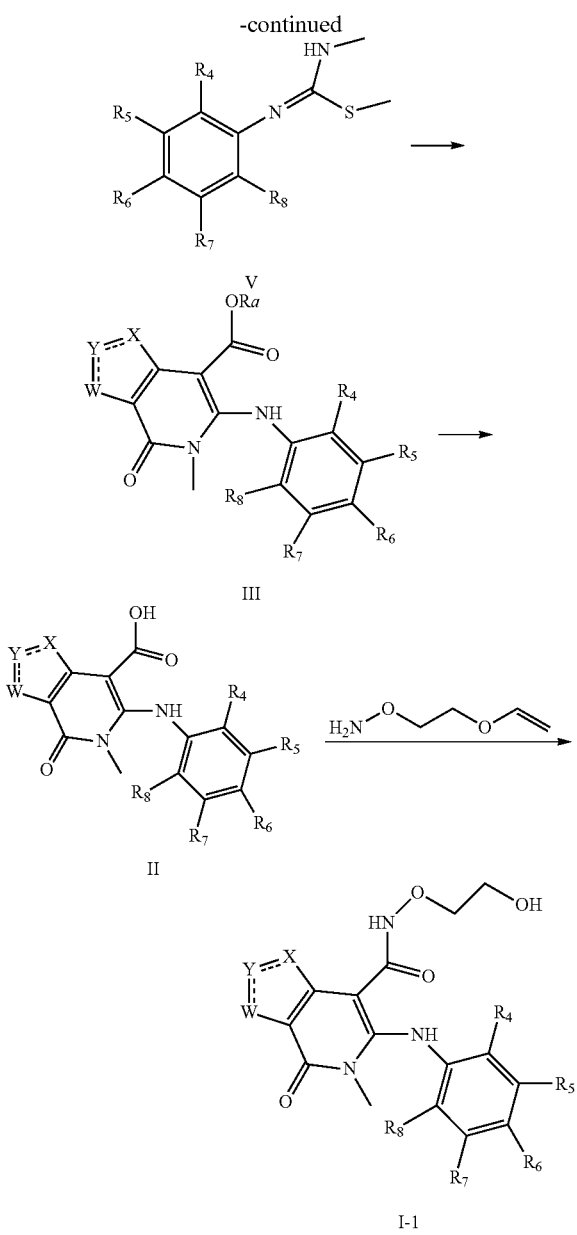

wherein $R_a$ and $R_b$ are each independently selected from the group consisting of hydrogen and $C_1$-$C_6$ alkyl;

$$X\text{---}Y\text{===}W$$

represents X—Y=W or X=Y—W;

X and W are independently selected from the group consisting of N, O, S, and $CR_2$;

Y is $CR_1$;

$R_1$ is selected from the group consisting of H and $C_1$-$C_6$ alkyl, wherein the alkyl is optionally substituted with a substituent independently selected from the group consisting of halo, hydroxyl, —$NH_2$, —NH($C_1$-$C_6$ alkyl), —N($C_1$-$C_6$ alkyl)$_2$, and $C_1$-$C_6$ heterocyclic group;

$R_2$ is selected from the group consisting of H and $C_1$-$C_6$ alkyl;

$R_4$, $R_5$, $R_6$, $R_7$, and $R_8$ are independently selected from the group consisting of H, halo, $SR_9$, and $OR_9$; and each $R_9$ is independently selected from the group consisting of hydrogen and $C_1$-$C_{10}$ alkyl.

In some embodiments of the present application, $R_a$ and $R_b$ are each independently $C_1$-$C_6$ alkyl. In some typical embodiments of the present application, $R_a$ and $R_b$ are each independently selected from the group consisting of methyl, ethyl, n-propyl, isopropyl, n-butyl, isobutyl, and tert-butyl; in some more typical embodiments, $R_a$ and $R_b$ are each independently selected from the group consisting of methyl, ethyl, and n-propyl; and in some still more typical embodiments, $R_a$ and $R_b$ are methyl or ethyl.

In some embodiments of the present application, X is O or S, and W is $CR_2$.

In some embodiments of the present application, $R_4$, $R_5$, $R_6$, $R_7$, and $R_8$ are independently selected from the group consisting of H and halo. In some typical embodiments of the present application, one of $R_4$ and $R_8$ is fluoro or chloro, and $R_6$ is iodo.

In some embodiments of the present application, $R_a$ and $R_b$ are each independently selected from the group consisting of methyl and ethyl; X is O; Y is CH; W is CH; $R_4$ is chloro; $R_6$ is iodo; and each of $R_5$, $R_7$, and $R_8$ is hydrogen.

In some embodiments of the present application, in the step 1), the compound of formula IV reacts with the compound of formula V in a first solvent selected from the group consisting of tetrahydrofuran, dichloromethane, ethyl acetate, N,N-dimethylformamide, acetone, N,N-dimethylacetamide, N-methyl pyrrolidone, dimethyl sulfoxide, and a mixture thereof; preferably, the first solvent is selected from the group consisting of tetrahydrofuran, N,N-dimethylformamide, acetone, N-methyl pyrrolidone, and a mixture thereof and more preferably, the first solvent is tetrahydrofuran, acetone, or a mixture thereof.

In some embodiments of the present application, the compound of formula IV reacts with the compound of formula V in the presence of a first base in the step 1); preferably, the first base is selected from the group consisting of NaHMDS, LiHMDS, KHMDS, lithium diisopropylamide, tert-butyl lithium, n-butyl lithium, potassium tert-butoxide, sodium methoxide, and a mixture thereof more preferably, the first base is selected from the group consisting of NaHMDS, LiHMDS, tert-butyl lithium, and a mixture thereof; and still more preferably, the first base is NaHMDS or LiHMDS.

In some embodiments of the present application, a molar ratio of the compound of formula IV to the first base in the step 1) is 1:1~5; preferably, the molar ratio of the compound of formula IV to the first base is 1:1~3; and more preferably, the molar ratio of the compound of formula IV to the first base is 1:1~1.5.

In some embodiments of the present application, a molar ratio of the compound of formula IV to the compound of formula V in the step 1) is 1~5:1; preferably, the molar ratio of the compound of formula IV to the compound of formula V in the step 1) is 1~3:1; and more preferably, the molar ratio of the compound of formula IV to the compound of formula V in the step 1) is 1.5~2:1.

In some embodiments of the present application, the compound of formula IV reacts with the compound of formula V at a temperature of 45° C. to 70° C. in the step 1); and preferably, the compound of formula IV reacts with the compound of formula V at a temperature of 50° C. to 65° C. in the step 1).

In some embodiments of the present application, the compound of formula III is hydrolyzed under the catalysis of a second base to obtain the compound of formula II in the step 2); preferably, the second base is selected from the group consisting of potassium carbonate, sodium carbonate, sodium hydroxide, potassium hydroxide, lithium hydroxide, and a mixture thereof; more preferably, the second base is selected from the group consisting of potassium carbonate and lithium hydroxide; and still more preferably, the second base is potassium carbonate.

In some embodiments of the present application, the compound of formula II reacts with O-(2-(vinyloxy)ethyl)hydroxylamine in the presence of a third base in the step 3); preferably, the third base is selected from the group consisting of NaHMDS, LiHMDS, KHMDS, lithium diisopropylamide, tert-butyl lithium, n-butyl lithium, potassium tert-butoxide, sodium methoxide, and a mixture thereof; more preferably, the third base is selected from the group consisting of NaHMDS, LiHMDS, and a mixture thereof; and still more preferably, the third base is NaHMDS.

In some embodiments of the present application, in the step 3), the compound of formula II reacts with O-(2-(vinyloxy)ethyl)hydroxylamine in a second solvent selected from the group consisting of tetrahydrofuran, dichloromethane, ethyl acetate, N,N-dimethylformamide, acetone, N,N-dimethylacetamide, N-methyl pyrrolidone, dimethyl sulfoxide, and a mixture thereof; preferably, the second solvent is selected from the group consisting of tetrahydrofuran, dichloromethane, N,N-dimethylformamide, acetone, and a mixture thereof; and more preferably, the second solvent is selected from the group consisting of N,N-dimethylformamide, tetrahydrofuran, and a mixture thereof.

In some embodiments of the present application, the hydrolysis in the step 3) is an acid-catalyzed hydrolysis; preferably, the acid is selected from the group consisting of hydrochloric acid, nitric acid, sulfuric acid, hydrobromic acid, trifluoroacetic acid, and a mixture thereof; more preferably, the acid is selected from the group consisting of hydrochloric acid, sulfuric acid, and hydrobromic acid; and still more preferably, the acid is hydrochloric acid.

In some embodiments of the present application, the present application further provides a method for preparing a compound of formula I-1, comprising 1) reacting a compound of formula IV with a compound of formula V in the presence of a first base and a first solvent to obtain a compound of formula III;

2) hydrolyzing the compound of formula III under the catalysis of a second base to obtain a compound of formula II; and 3) reacting the compound of formula II with O-(2-(vinyloxy)ethyl)hydroxylamine in the presence of a third base and a second solvent, followed by a further acid-catalyzed hydrolysis to obtain the compound of formula I-1,

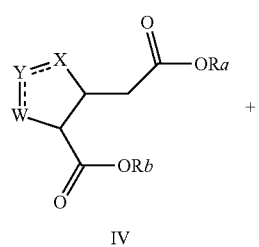

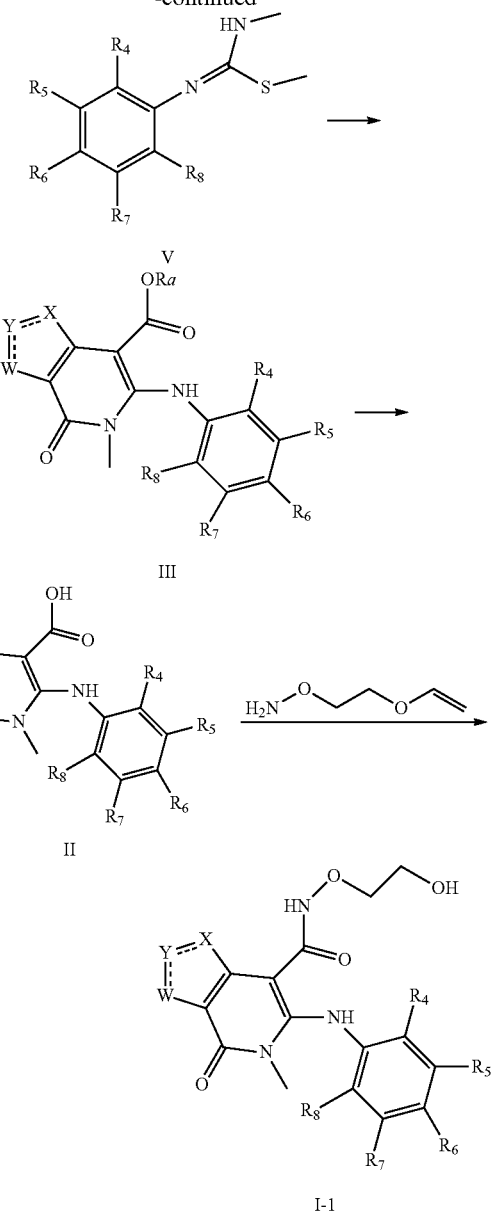

wherein $R_a$, $R_b$, $$X = Y = W,$$

X, W, Y, $R_4$, $R_5$, $R_6$, $R_7$, and $R_8$, the first base, the second base, the third base, the first solvent, the second solvent, and the acid are as defined hereinabove.

In still another aspect, the present application provides another method for preparing a compound of formula I-1, comprising a) reacting a compound of formula IV with a compound of formula V to obtain a compound of formula III; and b) reacting the compound of formula III with O-(2-(vinyloxy)ethyl)hydroxylamine followed by a hydrolysis to obtain the compound of formula I-1,

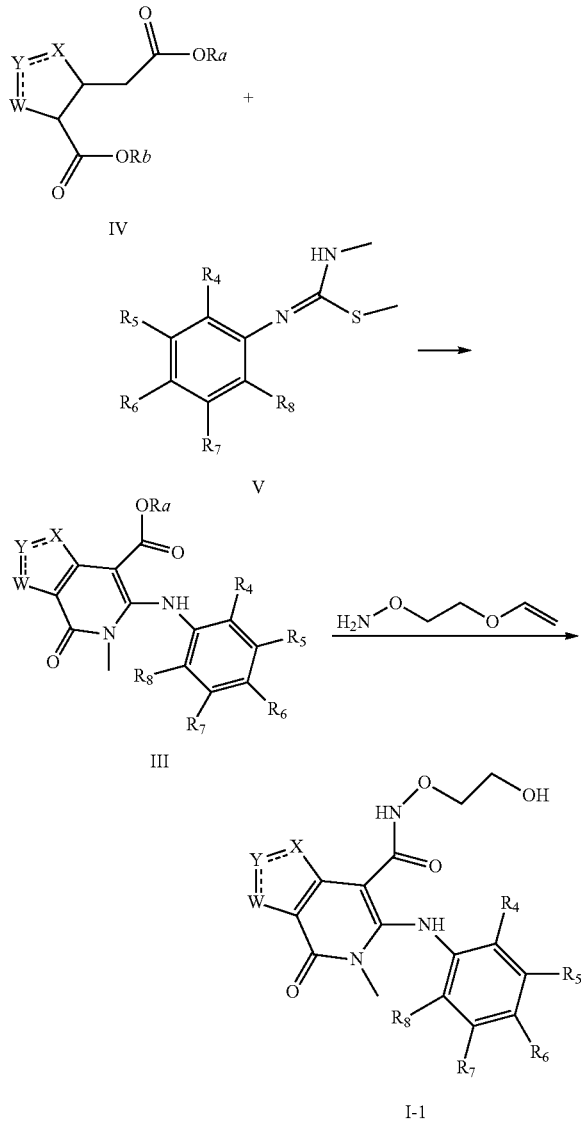

III

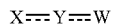

I-1 wherein $R_a$ and $R_b$ are each independently selected from the group consisting of hydrogen and $C_1$-$C_6$ alkyl;

$$X = Y = W$$

represents X—Y=W or X=Y—W;

X and W are independently selected from the group consisting of N, O, S, and $CR_2$;

Y is $CR_1$;

$R_1$ is selected from the group consisting of H and $C_1$-$C_6$ alkyl, wherein the alkyl is optionally substituted with a substituent independently selected from the group consisting of halo, hydroxyl, —$NH_2$, —$NH(C_1$-$C_6$ alkyl), —$N(C_1$-$C_6$ alkyl)$_2$, and $C_1$-$C_6$ heterocyclic group;

$R_2$ is selected from the group consisting of H and $C_1$-$C_6$ alkyl;

$R_4$, $R_5$, $R_6$, $R_7$, and $R_8$ are independently selected from the group consisting of H, halo, $SR_9$, and $OR_9$; and each $R_9$ is independently selected from the group consisting of hydrogen and $C_1$-$C_{10}$ alkyl.

In some embodiments of the present application, $R_a$ and $R_b$ are each independently $C_1$-$C_6$ alkyl. In some typical embodiments of the present application, $R_a$ and $R_b$ are each independently selected from the group consisting of methyl, ethyl, n-propyl, isopropyl, n-butyl, isobutyl, and tert-butyl; in some more typical embodiments, $R_a$ and $R_b$ are each independently selected from the group consisting of methyl, ethyl, and n-propyl; and in some still more typical embodiments, $R_a$ and $R_b$ are methyl or ethyl.

In some embodiments of the present application, X is O or S, and W is $CR_2$.

In some embodiments of the present application, $R_4$, $R_5$, $R_6$, $R_7$, and $R_8$ are independently selected from the group consisting of H and halo. In some typical embodiments of the present application, one of $R_4$ and $R_8$ is fluoro or chloro, and $R_6$ is iodo.

In a specific embodiment of the present application, $R_a$ and $R_b$ are each independently selected from the group consisting of methyl and ethyl; X is O; Y is CH; W is CH; $R_4$ is chloro; $R_6$ is iodo; and each of $R_5$, $R_7$, and $R_8$ is hydrogen.

In some embodiments of the present application, in the step a), the compound of formula IV reacts with the compound of formula V in a first solvent selected from the group consisting of tetrahydrofuran, dichloromethane, ethyl acetate, N,N-dimethylformamide, acetone, N,N-dimethylacetamide, N-methyl pyrrolidone, dimethyl sulfoxide, and a mixture thereof; preferably, the first solvent is selected from the group consisting of tetrahydrofuran, N,N-dimethylformamide, acetone, N-methyl pyrrolidone, and a mixture thereof; and more preferably, the first solvent is tetrahydrofuran, acetone, or a mixture thereof.

In some embodiments of the present application, the compound of formula IV reacts with the compound of formula V in the presence of a first base in the step a); preferably, the first base is selected from the group consisting of NaHMDS, LiHMDS, KHMDS, lithium diisopropylamide, tert-butyl lithium, n-butyl lithium, potassium tert-butoxide, sodium methoxide, and a mixture thereof; more preferably, the first base is selected from the group consisting of NaHMDS, LiHMDS, tert-butyl lithium, and a mixture thereof and still more preferably, the first base is NaHMDS or LiHMDS.

In some embodiments of the present application, a molar ratio of the compound of formula IV to the first base in the step a) is 1:1~5; preferably, the molar ratio of the compound of formula IV to the first base is 1:1~3; and more preferably, the molar ratio of the compound of formula IV to the first base is 1:1~1.5.

In some embodiments of the present application, a molar ratio of the compound of formula IV to the compound of formula V in the step a) is 1~5:1; preferably, the molar ratio of the compound of formula IV to the compound of formula V is 1~3:1; and more preferably, the molar ratio of the compound of formula IV to the compound of formula V is 1.5~2:1.

In some embodiments of the present application, the compound of formula IV reacts with the compound of formula V at a temperature of 45 to 70° C. in the step a); and preferably, the compound of formula IV reacts with the compound of formula V at a temperature of 50 to 65° C.

In some embodiments of the present application, the compound of formula III reacts with O-(2-(vinyloxy)ethyl) hydroxylamine in the presence of a third base in the step b); preferably, the third base is selected from the group consisting of NaHMDS, LiHMDS, KHMDS, lithium diisopropylamide, tert-butyl lithium, n-butyl lithium, potassium tert-butoxide, sodium methoxide, and a mixture thereof, more preferably, the third base is selected from the group consisting of NaHMDS, LiHMDS, and a mixture thereof; and still more preferably, the third base is NaHMDS.

In some embodiments of the present application, in the step b), the compound of formula III reacts with O-(2-(vinyloxy)ethyl)hydroxylamine in a second solvent selected from the group consisting of tetrahydrofuran, dichloromethane, ethyl acetate, N,N-dimethylformamide, acetone, N,N-dimethylacetamide, N-methyl pyrrolidone, dimethyl sulfoxide, and a mixture thereof; preferably, the second solvent is selected from the group consisting of tetrahydrofuran, dichloromethane, N,N-dimethylformamide, acetone, and a mixture thereof; and more preferably, the second solvent is selected from the group consisting of N,N-dimethylformamide, tetrahydrofuran, and a mixture thereof.

In some embodiments of the present application, the hydrolysis is acid-catalyzed hydrolysis in the step b); preferably, the used acid is selected from the group consisting of hydrochloric acid, nitric acid, sulfuric acid, hydrobromic acid, trifluoroacetic acid, and a mixture thereof; more preferably, the acid is selected from the group consisting of hydrochloric acid, sulfuric acid, and hydrobromic acid; and still more preferably, the acid is hydrochloric acid.

In some embodiments of the present application, a molar ratio of the compound of formula III to O-(2-(vinyloxy)ethyl)hydroxylamine in the step b) is 1:1~3; and preferably, the molar ratio of the compound of formula III to O-(2-(vinyloxy)ethyl)hydroxylamine is 1:1~1.5.

In some embodiments of the present application, a molar ratio of the compound of formula III to the third base in the step b) is 1:2~5; and preferably, the molar ratio of the compound of formula III to the third base is 1:4.

In some embodiments of the present application, the reaction temperature in the step b) is 0 to 10° C.; and preferably, the reaction is carried out at the reaction temperature of 0 to 5° C. and under the protection of an inert gas, such as nitrogen.

In yet another aspect, the present application provides a compound of formula V-a,

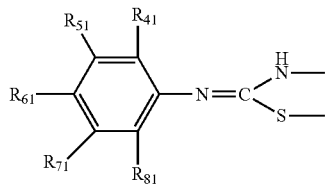

V-a wherein $R_{41}$ is fluoro or chloro, $R_{61}$ is iodo, and each of $R_{51}$, $R_{71}$, and $R_{81}$ is hydrogen.

In some embodiments of the present application, $R_{41}$ is chloro, $R_{61}$ is iodo, and each of $R_{51}$, $R_{71}$, and $R_{81}$ is hydrogen.

In another aspect, the present application provides use of a compound of formula V in the preparation of a compound of formula III. In some typical embodiments of the present application, the compound of formula V is a compound of formula V-a.

In still another aspect, the present application further provides a method for preparing a compound of formula V, comprising reacting compound of formula VII with a compound of formula VIII to obtain a compound of formula VI; and reacting the compound of formula VI with a methylating reagent to obtain the compound of formula V

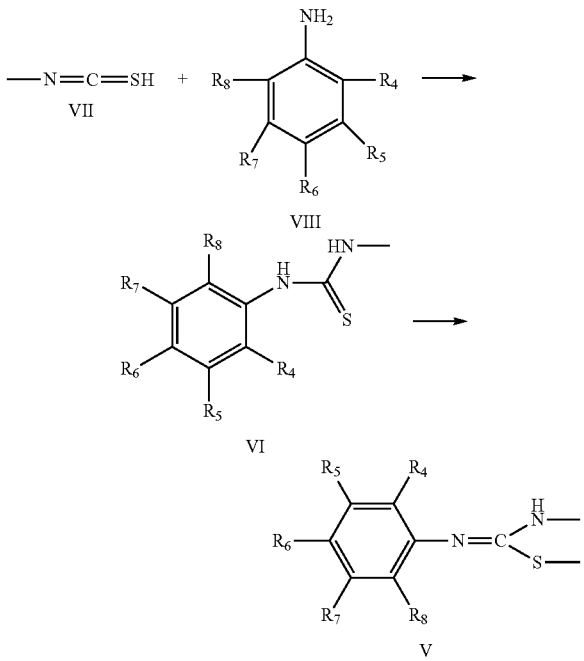

wherein $R_4$, $R_5$, $R_6$, $R_7$, and $R_8$ are independently selected from the group consisting of H, halo, $SR_9$, and $OR_9$; and each $R_9$ is independently selected from the group consisting of hydrogen and $C_1$-$C_{10}$ alkyl.

In some embodiments of the present application, $R_4$, $R_5$, $R_6$, $R_7$, and $R_8$ are independently selected from the group consisting of H and halo. In some typical embodiments of the present application, one of $R_4$ and $R_8$ is fluoro or chloro, and $R_6$ is iodo. In some more typical embodiments of the present application, $R_4$ is chloro, $R_6$ is iodo, and each of $R_5$, $R_7$, and $R_8$ is hydrogen.

In some embodiments of the present application, the compound of formula VII reacts with the compound of formula VIII in a third solvent selected from the group consisting of methanol, ethanol, isopropanol, tetrahydrofuran, ethyl acetate, acetone, N,N-dimethylformamide, dimethyl sulfoxide, N-methyl pyrrolidone, and a mixture thereof; preferably, the third solvent is selected from the group consisting of methanol, ethanol, tetrahydrofuran, and N,N-dimethylformamide; and more preferably, the third solvent is ethanol.

In some embodiments of the present application, a molar ratio of the compound of formula VII to the compound of formula VIII is 1~4:1; preferably, the molar ratio of the compound of formula VII to the compound of formula VIII is 1~2.5:1; and more preferably, the molar ratio of the compound of formula VII to the compound of formula VIII is 1~1.8:1.

In some embodiments of the present application, the compound of formula VII reacts with the compound of formula VIII at a reaction temperature of 45 to 85° C.; preferably, the compound of formula VII reacts with the compound of formula VIII at the reaction temperature of 60 to 80° C.; and more preferably, the compound of formula VII reacts with the compound of formula VIII at the reaction temperature of 75 to 80° C.

In some embodiments of the present application, the methylating reagent is selected from the group consisting of iodomethane, dimethyl sulfate, dimethyl carbonate, and a mixture thereof; and preferably is iodomethane.

In some embodiments of the present application, the compound of formula VI reacts with the methylating reagent in a fourth solvent selected from the group consisting of tetrahydrofuran, dichloromethane, ethyl acetate, N,N-dimethylformamide, acetone, N-methyl pyrrolidone, dimethyl sulfoxide, and a mixture thereof; preferably, the fourth solvent is selected from the group consisting of tetrahydrofuran, dichloromethane, and acetone; and more preferably, the fourth solvent is acetone.

In some embodiments of the present application, the compound of formula VI reacts with the methylating reagent in the presence of a fourth base; preferably, the fourth base is selected from the group consisting of potassium carbonate, sodium carbonate, cesium carbonate, sodium hydroxide, potassium hydroxide, lithium hydroxide, and a mixture thereof; more preferably, the fourth base is selected from the group consisting of potassium carbonate, sodium carbonate, and cesium carbonate; and still more preferably, the fourth base is potassium carbonate.

In some embodiments of the present application, a molar ratio of the compound of formula VI to the methylating reagent is 1:1~5; preferably, the molar ratio of the compound of formula VI to the methylating reagent is 1:1~3; and more preferably, the molar ratio of the compound of formula VI to the methylating reagent is 1:1~1.5.

In some embodiments of the present application, the compound of formula VI reacts with the methylating reagent at a reaction temperature of 25° C. to 60° C.; preferably, the compound of formula VI reacts with the methylating reagent at the reaction temperature of 35 to 55° C.; and more preferably, the compound of formula VI reacts with the methylating reagent at the reaction temperature of 45 to 50° C.

In some embodiments of the present application, the present application further provides a method for preparing a compound of formula V, comprising reacting a compound of formula VII with a compound of formula VIII in a third solvent to obtain a compound of formula VI; and reacting the compound of formula VI with iodomethane in the presence of a fourth base and a fourth solvent to obtain the compound of formula V

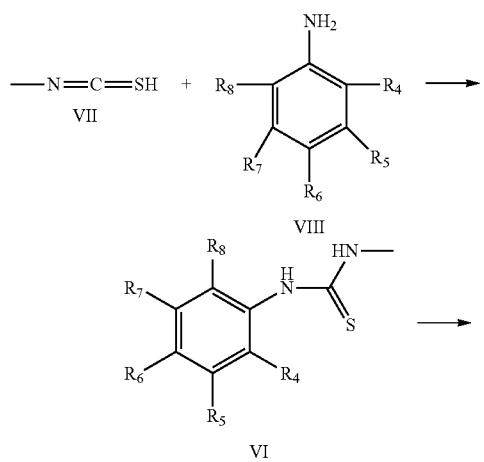

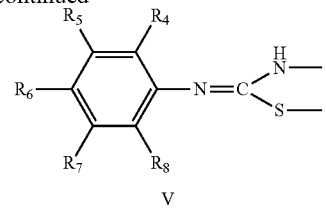

wherein $R_4$, $R_5$, $R_6$, $R_7$, and $R_8$ as well as the fourth base, the third solvent, and the fourth solvent are as defined hereinabove.

In the present application, the compound of formula IV can be commercially available, and can be also prepared from dialkyl 3-oxoglutarate as a starting material with reference to the method in step A of Example 1 of CN102020651A. For example, in some specific embodiments, a compound of formula IV-2 can be prepared by the following method:

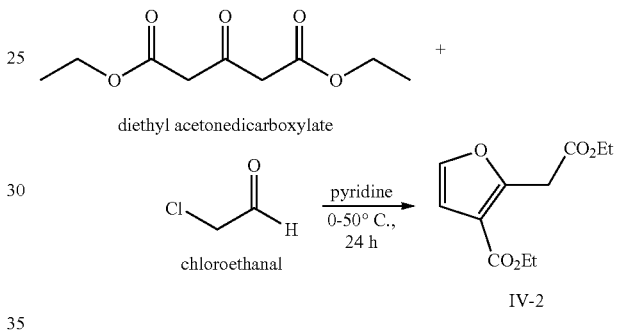

9.89 mol of diethyl acetonedicarboxylate and 3.8 L of anhydrous pyridine were added to a 10 L three-necked flask, and the resulting solution was cooled to 0° C. in an ice water bath. 11.88 mol of chloroethanal (40% aqueous solution of chloroethanal) was added dropwise under stirring, and the temperature of the reaction system was controlled no more than 10° C. during the dropwise addition. The reaction mixture was warmed to 50° C. under stirring, and stirred for 24 hr at this temperature. Then, 20 L of ethyl acetate was added. The mixture was washed sequentially with 2 N HCl (20 L×2) and a saturated NaCl solution (10 L×2), then dried over anhydrous $Na_2SO_4$, filtered, and evaporated under reduced pressure to remove the solvent. The residue was distilled under reduced pressure (115-123° C./5 mmHg) to afford a compound of formula IV-2 as colorless liquid (yield of 59%).

In the present application, unless otherwise specified, NaHMDS refers to sodium bis(trimethylsilyl)amide, LiHMDS refers to lithium bis(trimethylsilyl)amide, KHMDS refers to potassium bis(trimethylsilyl)amide, THF refers to tetrahydrofuran, and DMF refers to N,N-dimethylformamide.

The present application provides a new process for preparing a compound of formula III, which has at least one of the following advantages: (1) the reaction materials, especially a compound of formula V, are easy to store and have good stability, and accordingly they are not easy to introduce impurities into the reaction, and no additional purification is required to remove impurities, thereby reducing the production costs; and (2) a mild base is used as a catalyst so as to reduce the potential safety hazards in production. Therefore, the preparation process of the present application contributes to a large-scale industrial production of the compound of formula III.

EXAMPLES

Embodiments of the present application are illustrated with reference to the following specific examples, but the protection scope of the present application is not limited to the scope of the following examples. The used reagents all are commercially available products.

Example 1

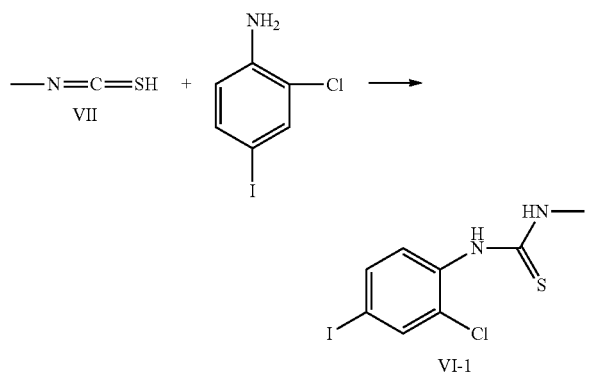

To a 5 L glass reactor were added 600 g of methyl isothiocyanate, 1.2 kg of 2-chloro-4-iodoaniline, and 1.5 L of ethanol, warmed to about 80° C., reacted for about 12 hr under reflux, and then maintained at 80° C. To the reaction system was added dropwise 1 L of ethanol. After the dropwise addition was completed, the reaction mixture was hot-transferred to 1.5 L of ethanol at a temperature of 0° C. to 5° C. under stirring, and a large amount of off-white solid was precipitated out, continuously stirred for additional 3-4 hr, filtered, and dried for 5-6 hr in vacuo at 45° C. to 50° C. to afford the compound VI-1 as off-white solid (1.252 kg) (yield of 81.1%). $^1$H-NMR (300 MHz, DMSO-$d_6$) δ: 9.18 (1H), 7.91 (1H), 7.85 (1H), 7.64-7.67 (1H), 7.44-7.46 (1H), 2.91-2.92 (3H). [M+H]$^+$: 326.9207

Example 2

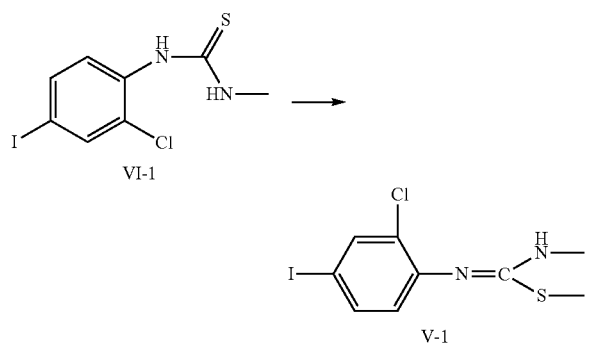

To a 5 L glass reactor were added 1.1 kg of the compound VI-1, 745 g of $K_2CO_3$, and 4 L of acetone, and thereto was added dropwise 570 g of $CH_3I$ under stirring at 20° C. to 25° C. After the dropwise addition was completed, the reaction mixture was warmed to a temperature of 45° C. to 50° C., and reacted for 3-4 hr under reflux. After the reaction was completed, the reaction mixture was filtered to remove insoluble substances. The filtrate was evaporated under reduced pressure to remove about half of acetone, and then slowly poured into 10 L of ice water under vigorous stirring. A large amount of solid was precipitated out, filtered, and dried for 6-7 hr in vacuo at 50° C. to afford 1.134 kg of lilac solid. Thereto was added 2 L of methanol, and the resulting mixture was warmed to about 65° C., stirred for about 0.5 hr, cooled for crystallization, stirred for about 2 hr at −5° C. to 0° C., filtered, and dried for 4-5 hr in vacuo at 45° C. to 50° C. to afford the compound V-1 as lilac solid (yield of 85.3%). $^1$H-NMR (300 MHz, DMSO-$d_6$) δ: 7.67 (1H), 7.45-7.48 (1H), 6.63-6.66 (1H), 2.81-2.83 (3H), 2.31 (3H), 6.77-6.78 (1H). [M+H]$^+$: 340.9356.

Example 3

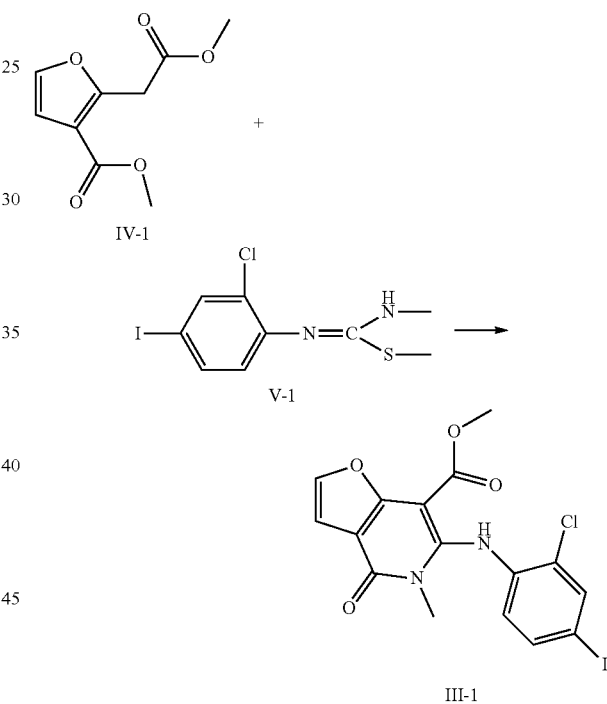

To a 2 L glass reactor was added 500 mL of acetone, and thereto was added 255 mL of a solution of LiHMDS in THF having a concentration of 2 mol/L under stirring at room temperature under nitrogen atmosphere. After the addition was completed, to the reaction mixture was added dropwise a solution of 100.5 g of the compound of formula IV-1 in 150 mL of acetone. After the addition was completed, the reaction mixture was warmed to 50° C. to 55° C., and then a solution of 86.5 g of a compound of formula V-1 in 300 mL of acetone was added dropwise to the above reaction mixture at this temperature. After the addition was completed, the reaction mixture was reacted for 4 hr. At 0° C. to 5° C., 2 N HCl was added dropwise to pH of 3 to 4. Then, the mixture was poured into 2 L of water, and extracted with 3 L of ethyl acetate. The organic phase was combined, and rotary-evaporated to afford dark yellow solid. Thereto was added 400 mL of methanol, heated to reflux, and continuously stirred for additional about 1 hr. After stopping the heating, the reaction mixture was cooled for crystallization, stirred for 1 hr at 0° C. to 5° C., and filtered. The resulting solid was dried for 5 hr at 50° C. to 60° C. to afford a compound of formula III-1 as light yellow powder (yield of 66.5%).

Example 4

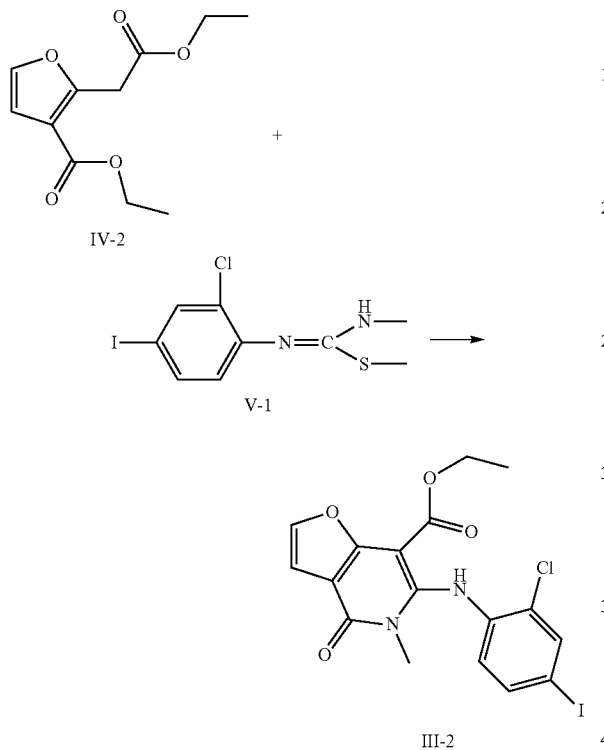

To a 5 L glass reactor was added 1.4 L of THF, and thereto was added 800 mL of a solution of NaHMDS in THF having a concentration of 2 mol/L under stirring at room temperature under nitrogen atmosphere. After the addition was completed, to the reaction mixture was added dropwise a solution of 275.5 g of a compound of formula IV-2 in 250 mL of THF. After the addition was completed, the reaction mixture was warmed to 60° C. to 65° C., and then a solution of 275.7 g of a compound of formula V-1 in 500 mL of THF was added dropwise to the above reaction mixture at this temperature. After the addition was completed, the reaction mixture was reacted for 6 hr. At 0° C. to 5° C., 2 N HCl solution was added dropwise to pH of 3 to 4. Then, the mixture was poured into 5 L of water, and extracted with 7 L of ethyl acetate. The organic phase was combined, and rotary-evaporated to afford dark yellow solid. Thereto was added 1 L of methanol, heated to reflux, and continuously stirred for additional about 1 hr. After stopping heating, the reaction mixture was cooled for crystallization, stirred for 1 hr at 0° C. to 5° C., and filtered. The resulting solid was dried for 6 hr at 50° C. to 60° C. to afford a compound of formula III-2 as light yellow powder (yield of 62.9%).

Example 5

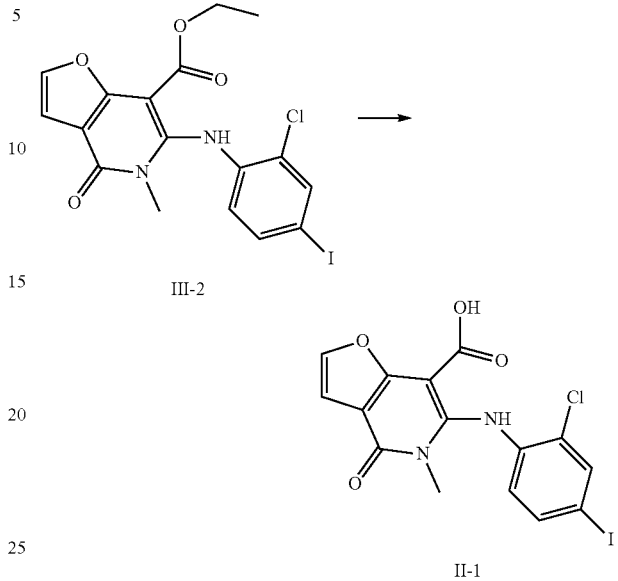

To a 10 L glass reactor were added 300 g of a compound of formula III-2, 3 L of tetrahydrofuran, and 2.25 L of methanol, and stirred at room temperature. To the reaction system was added a solution of 315 g of potassium carbonate in 2.25 L of water. The reaction mixture was heated to 60° C. to 65° C., and reacted for 10 hr. Then, the mixture was washed with ethyl acetate twice after the addition of water. The aqueous layer was separated, and acidified with 2 N HCl. Solid was precipitated out, filtered, and dried to afford a compound of formula II-1 (yield of 65.0%).

Example 6

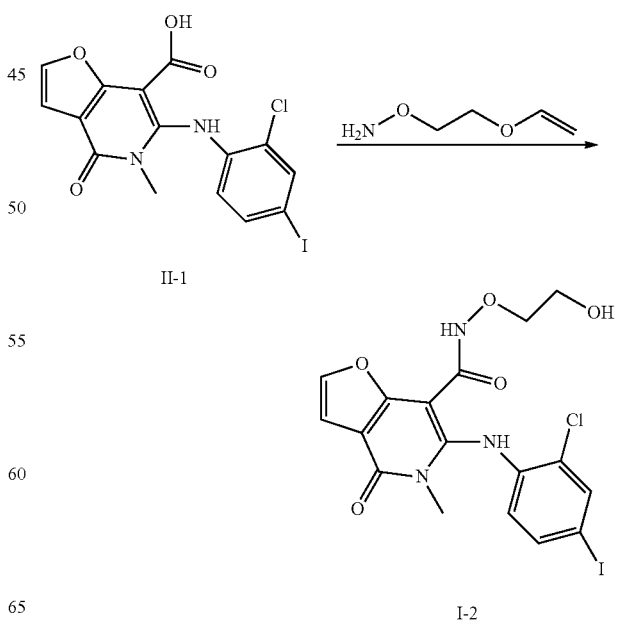

To a 3 L three-necked flask were added 50.0 g of a compound of formula II-1 and 250 mL of DMF, and thereto was added O-(2-(vinyloxy)ethyl)hydroxylamine under nitrogen atmosphere at 0° C. to 5° C., followed by the slow addition of 225 mL of a solution of NaHMDS in tetrahydrofuran having a concentration of 2 mol/L, and then reacted for about 7 hr at 0° C. to 5° C. Then, 225 mL of 6 N hydrochloric acid solution was added dropwise at about 0° C. After the dropwise addition was completed, the reaction mixture was reacted for 4 hr at 0° C. to 5° C. After the reaction was completed, the mixture was poured into 1 L of water, and extracted with 1.5 L of ethyl acetate. The organic phase was combined, and concentrated under reduced pressure to afford dark yellow solid. Thereto was added about 100 mL of ethanol, slurried for 10 hr at room temperature, and filtered to afford light yellow solid, which was dried for 6 hr in vacuo at 45° C. to 50° C. to afford a compound of formula I-2 (yield of 88.1%). [M+H]$^+$: 503.9803.

Example 7

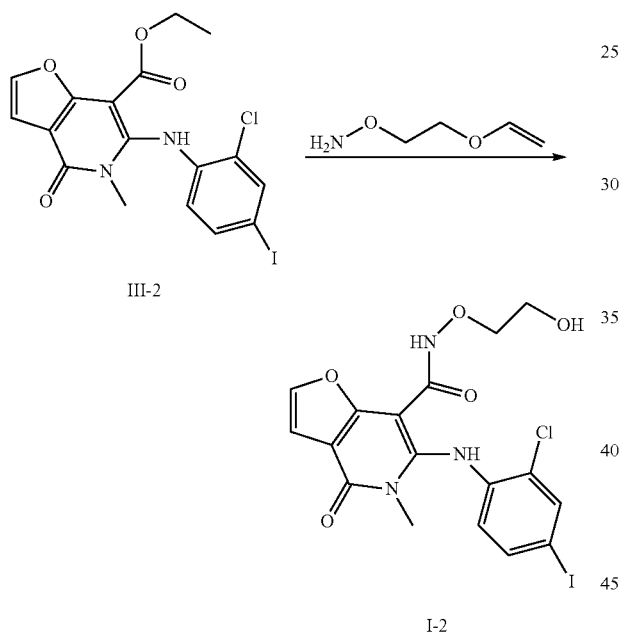

To a 5 L glass reactor were added 225.4 g of a compound of formula III-2 and 1350 mL of tetrahydrofuran, and thereto was added 73.6 g of O-(2-(vinyloxy)ethyl)hydroxylamine under nitrogen atmosphere at 0° C. to 5° C., followed by the slow addition of 950 mL of a solution of NaHMDS in tetrahydrofuran having a concentration of 2 mol/L. After the addition was completed, the reaction mixture was reacted for 6 to 7 hr at 0° C. to 5° C. At this time, the compound of formula III-2 was completely consumed. At 0° C., 950 mL of 6 N HCl solution was added dropwise. After the dropwise addition was completed, the reaction mixture was reacted for 3 to 4 hr at 0° C. to 5° C. The reaction mixture was poured into 5 L of water, and extracted with 7 L of ethyl acetate. The organic phase was combined, and rotary-evaporated to afford dark yellow solid. Thereto was added about 300 mL of ethanol, slurried for 10 to 12 hr at room temperature, and filtered to afford light yellow solid, which was dried for 5 to 6 hr in vacuo at 45° C. to 50° C. to afford a compound of formula I-2 (yield of 92.1%). HPLC: 98.90% purity.

What is claimed is:

1. A method for preparing a compound of formula III, comprising reacting a compound of formula IV with a compound of formula V,

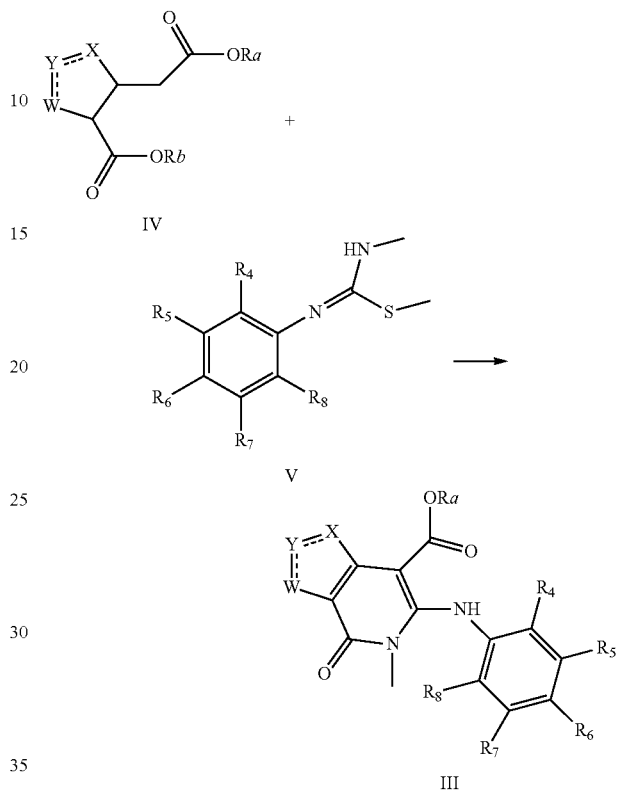

wherein R$_a$ and R$_b$ are each independently selected from the group consisting of hydrogen and C$_1$-C$_6$ alkyl;

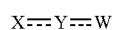

represents X—Y=W or X=Y—W;

X and W are independently selected from the group consisting of N, O, S, and CR$_2$;

Y is CR$_1$; and

R$_1$ is selected from the group consisting of H and C$_1$-C$_6$ alkyl, wherein the alkyl is optionally substituted with a substituent independently selected from the group consisting of halo, hydroxyl, —NH$_2$, —NH(C$_1$-C$_6$ alkyl), —N(C$_1$-C$_6$ alkyl)$_2$ and C$_1$-C$_6$ heterocyclic group;

R$_2$ is selected from the group consisting of H and C$_1$-C$_6$ alkyl;

R$_4$, R$_5$, R$_6$, R$_7$, and R$_8$ are independently selected from the group consisting of H, halo, SR$_9$, and OR$_9$; and each R$_9$ is independently selected from the group consisting of hydrogen and C$_1$-C$_{10}$ alkyl.

2. The method according to claim 1, wherein

R$_a$ and R$_b$ are each independently selected from the group consisting of methyl, ethyl, n-propyl, isopropyl, n-butyl, isobutyl, and tert-butyl;

Y is O or S;

W is CR$_2$; and

R$_4$, R$_5$, R$_6$, R$_7$, and R$_8$ are independently selected from the group consisting of H and halo.

3. The method according to claim 1, wherein $R_a$ and $R_b$ are each independently selected from the group consisting of methyl and ethyl; X is O; Y is CH; W is CH; $R_4$ is chloro; $R_6$ is iodo; and each of $R_5$, $R_7$, and $R_8$ is hydrogen.

4. The method according to claim 1, wherein the compound of formula IV reacts with the compound of formula V in a first solvent selected from the group consisting of tetrahydrofuran, dichloromethane, ethyl acetate, N,N-dimethylformamide, acetone, N,N-dimethylacetamide, N-methyl pyrrolidone, dimethyl sulfoxide, and a mixture thereof.

5. The method according to claim 1, wherein the compound of formula IV reacts with the compound of formula V in the presence of a first base.

6. The method according to claim 5, comprising using a molar ratio of the compound of formula IV to the first base that is 1:1~5.

7. The method according to claim 1, comprising using a molar ratio of the compound of formula IV to the compound of formula V that is 1~5:1.

8. A method for preparing a compound of formula I-1, comprising:

1) reacting a compound of formula IV with a compound of formula V to obtain a compound of formula III:

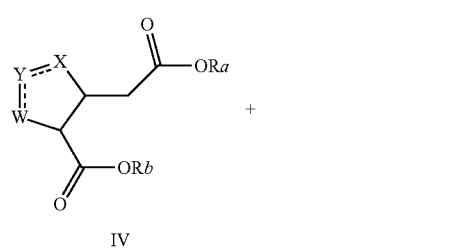

IV

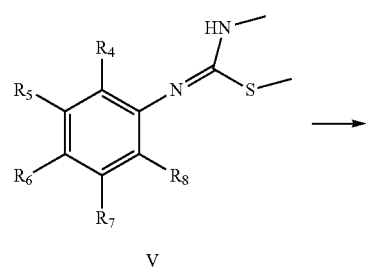

V

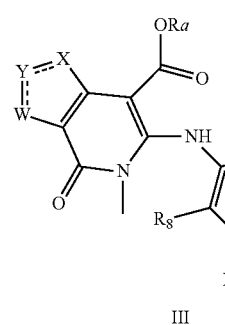

III 2) hydrolyzing the compound of formula III to obtain a compound of formula II

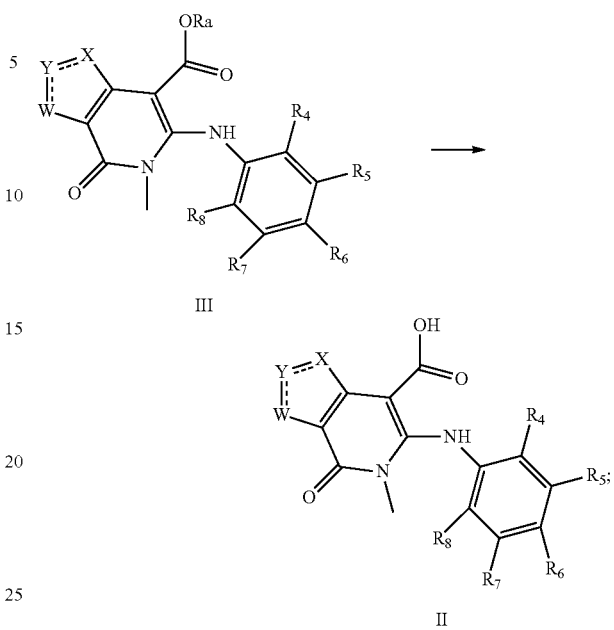

and 3) reacting the compound of formula II with O-(2-(vinyloxy)ethyl)hydroxylamine, followed by hydrolysis to obtain the compound of formula I-1,

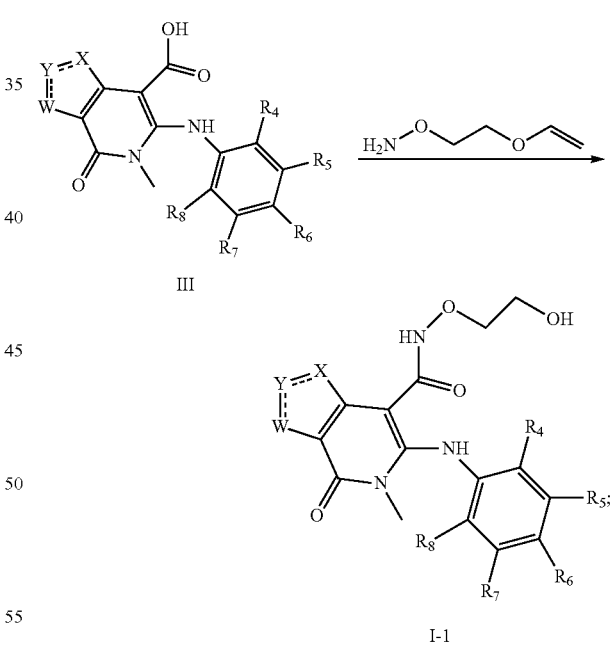

wherein $R_a$ and $R_b$ are each independently selected from the group consisting of hydrogen and $C_1$-$C_6$ alkyl;

$$X\text{---}Y\text{---}W,$$

represents X—Y=W or X=Y—W;
X and W are independently selected from the group consisting of N, O, S, and $CR_2$;

Y is CR$_1$; and

R$_1$ is selected from the group consisting of H and C$_1$-C$_6$ alkyl, wherein the alkyl is optionally substituted with a substituent independently selected from the group consisting of halo, hydroxyl, —NH$_2$, —NH(C$_1$-C$_6$ alkyl), —N(C$_1$-C$_6$ alkyl)$_2$ and C$_1$-C$_6$ heterocyclic group;

R$_2$ is selected from the group consisting of H and C$_1$-C$_6$ alkyl;

R$_4$, R$_5$, R$_6$, R$_7$, and R$_8$ are independently selected from the group consisting of H, halo, SR$_9$, and OR$_9$; and each R$_9$ is independently selected from the group consisting of hydrogen and C$_1$-C$_{10}$ alkyl.

9. A method for preparing a compound of formula I-1, comprising:

a) reacting a compound of formula IV with a compound of formula V to obtain a compound of formula III:

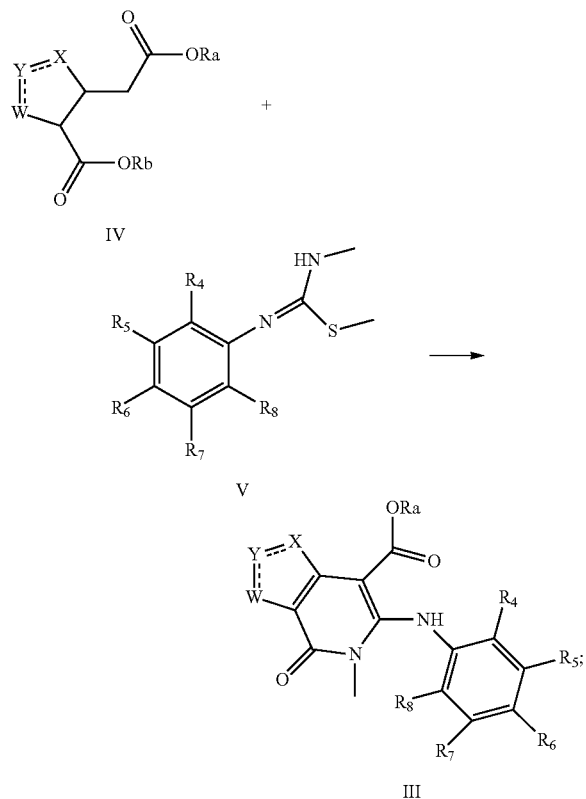

and b) reacting the compound of formula III with O-(2-(vinyloxy)ethyl)hydroxylamine, followed by hydrolysis to obtain the compound of formula I-1,

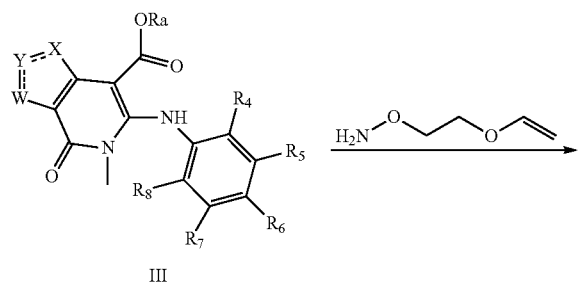

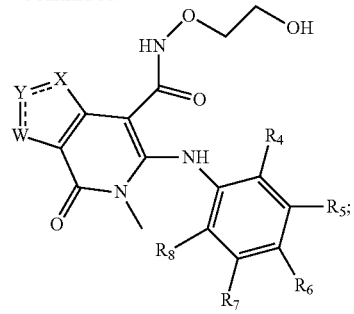

wherein R$_a$ and R$_b$ are each independently selected from the group consisting of hydrogen and C$_1$-C$_6$ alkyl;

$$X\text{---}Y\text{---}W$$

represents X—Y=W or X=Y—W;

X and W are independently selected from the group consisting of N, O, S, and CR$_2$;

Y is CR$_1$; and

R$_1$ is selected from the group consisting of H and C$_1$-C$_6$ alkyl, wherein the alkyl is optionally substituted with a substituent independently selected from the group consisting of halo, hydroxyl, —NH$_2$, —NH(C$_1$-C$_6$ alkyl), —N(C$_1$-C$_6$ alkyl)$_2$ and C$_1$-C$_6$ heterocyclic group;

R$_2$ is selected from the group consisting of H and C$_1$-C$_6$ alkyl;

R$_4$, R$_5$, R$_6$, R$_7$, and R$_8$ are independently selected from the group consisting of H, halo, SR$_9$, and OR$_9$; and each R$_9$ is independently selected from the group consisting of hydrogen and C$_1$-C$_{10}$ alkyl.

10. The method according to claim 4, wherein the first solvent is selected from the group consisting of tetrahydrofuran, N,N-dimethylformamide, acetone, N-methyl pyrrolidone, and a mixture thereof.

11. The method according to claim 10, wherein the first solvent is tetrahydrofuran or acetone, or a mixture thereof.

12. The method according to claim 5, wherein the first base is selected from the group consisting of NaHMDS, LiHMDS, KHMDS, lithium diisopropylamide, tert-butyl lithium, n-butyl lithium, potassium tert-butoxide, sodium methoxide, and a mixture thereof.

13. The method according to claim 12, wherein the first base is selected from the group consisting of NaHMDS, LiHMDS, tert-butyl lithium, and a mixture thereof.

14. The method according to claim 13, wherein the first base is NaHMDS or LiHMDS.

15. The method according to claim 6, wherein the molar ratio of the compound of formula IV to the first base is 1:1~3.

16. The method according to claim 15, wherein the molar ratio of the compound of formula IV to the first base is 1:1~1.5.

17. The method according to claim 7, wherein the molar ratio of the compound of formula IV to the compound of formula V is 1~3:1.

18. The method according to claim 17, wherein the molar ratio of the compound of formula IV to the compound of formula V is 1.5~2:1.

* * * * *